US012778994B2

(12) United States Patent
Sawada et al.

(10) Patent No.: US 12,778,994 B2
(45) Date of Patent: Nov. 3, 2026

(54) AGENT FOR REGULATING FEMALE HORMONE SECRETION AND AGENT FOR ALLEVIATING UNPLEASANT SYMPTOMS

(71) Applicants: Asahi Group Holdings, Ltd., Tokyo (JP); Tokushima University, Tokushima (JP)

(72) Inventors: Daisuke Sawada, Kanagawa (JP); Shigeru Fujiwara, Kanagawa (JP); Tomonori Sugawara, Kanagawa (JP); Kazuhito Rokutan, Tokushima (JP); Kensei Nishida, Tokushima (JP); Yuki Kuwano, Tokushima (JP)

(73) Assignees: ASAHI GROUP HOLDINGS, LTD., Tokyo (JP); TOKUSHIMA UNIVERSITY, Tokushima (JP)

( * ) Notice: Subject to any disclaimer, the term of this patent is extended or adjusted under 35 U.S.C. 154(b) by 773 days.

(21) Appl. No.: 17/626,622

(22) PCT Filed: Jul. 17, 2020

(86) PCT No.: PCT/JP2020/027754
§ 371 (c)(1),
(2) Date: Jan. 12, 2022

(87) PCT Pub. No.: WO2021/015104
PCT Pub. Date: Jan. 28, 2021

(65) Prior Publication Data

US 2022/0257676 A1 Aug. 18, 2022

(30) Foreign Application Priority Data

Jul. 24, 2019 (JP) ................................ 2019-135979

(51) Int. Cl.
*A61K 35/747* (2015.01)
*A61P 15/00* (2006.01)
*A61P 17/10* (2006.01)
*A61P 25/20* (2006.01)
*A61P 25/22* (2006.01)
*A61P 25/24* (2006.01)

(52) U.S. Cl.
CPC ............ *A61K 35/747* (2013.01); *A61P 15/00* (2018.01); *A61P 17/10* (2018.01); *A61P 25/20* (2018.01); *A61P 25/22* (2018.01); *A61P 25/24* (2018.01)

(58) Field of Classification Search
CPC ........ A61K 35/747; A61P 15/00; A61P 25/24; A61P 17/10
See application file for complete search history.

(56) References Cited

U.S. PATENT DOCUMENTS 7,125,911 B2 10/2006 Nagashima et al.
7,312,067 B2 * 12/2007 Samuelsson ......... A61K 9/0036 424/431
9,386,786 B2 7/2016 Kimura et al.
10,245,291 B2 * 4/2019 Nakamura ................ A61P 3/08
2002/0151600 A1 10/2002 Nagashima
2004/0039065 A1 2/2004 Nagashima et al.
2004/0048933 A1 3/2004 Nagashima et al.
2009/0311353 A1 12/2009 Kimura et al.
2010/0074976 A1 3/2010 Fowler et al.
2011/0070326 A1 3/2011 Fowler et al.
2012/0142786 A1 6/2012 Goralczyk et al.
2012/0277302 A1 11/2012 Kimura et al.
2012/0277303 A1 11/2012 Kimura et al.
2015/0283187 A1 10/2015 Sawada et al.
2017/0312232 A1 * 11/2017 Vitetta .................. A23L 33/135
2018/0235260 A1 8/2018 Kimura et al.

FOREIGN PATENT DOCUMENTS

JP 2007-197334 8/2007
JP 2009-51835 3/2009
JP 2010-500306 1/2010
JP 2014-158488 9/2014
WO 2018/073963 4/2018

OTHER PUBLICATIONS

Freeman EW. Treatment of depression associated with the menstrual cycle: premenstrual dysphoria, postpartum depression, and the perimenopause. Dialogues Clin Neurosci. 2002;4:177-191.*
Kluk J. Acne and the menstrual cycle. https://drjustinekluk.com/notebook/acne-and-the-menstrual-cycle/. 2018;1-2.*
Bagatin et al. Adult female acne: a guide to clinical practice. An Bras Dermatol. 2019;94(1):62-75.*
Daisuke Sawada et al., "Daily intake of *Lactobacillus gasseri* CP2305 relieves fatigue and stress-related symptoms in male university Ekiden runners: A double-blind, randomized, and placebo-controlled clinical trial", Journal of Functional Foods, vol. 57, pp. 465-476, 2019.
K. Nishida et al., "Para-psychobiotic Lactobacillus gasseri CP2305 ameliorates stress-related symptoms and sleep quality", Journal of Applied Microbiology, vol. 123, No. 6, Sep. 26, 2017 pp. 1561-1570.
Extended European Search Report issued Jun. 26, 2023 in corresponding European Patent Application No. 20843481.1.
International Search Report (ISR) issued Oct. 6, 2020 in International (PCT) Application No. PCT/JP2020/027754.
Kensei Nishida et al., "Daily administration of paraprobiotic *Lactobacillus gasseri* CP2305 ameliorates chronic stress-associated symptoms in Japanese medical students", Journal of Functional Foods, vol. 36, pp. 112-121, 2017, cited in ISR.

(Continued)

*Primary Examiner* — Lynn Y Fan
(74) *Attorney, Agent, or Firm* — Wenderoth, Lind & Ponack, L.L.P.

(57) ABSTRACT

[Problem] The purpose of the present invention is to provide a novel technology capable of regulating female hormone secretion. [Solution] Provided is an agent for regulating female hormone secretion, which contains the *lactobacillus* strain *Lactobacillus gasseri* strain CP2305 (accession No.: FERM PB-11331), a treated product of said *lactobacillus* strain, or extracts thereof.

8 Claims, 3 Drawing Sheets

(56) References Cited

OTHER PUBLICATIONS

Kaoru Kagawa, et al., "The Relationship between Premenstrual Symptoms and Resilience, Cognition for menstruation, Coping in Young Females", Jpn. J. Psychosom. Med., vol. 53, No. 8, pp. 748-756, 2013, together with abstract, cited in ISR.

http://www.jsog.or.jp/modules/diseases/index.php?content_id=13, entirety, p. 1, (Japan society of obstetrics and gynecology Web site, Japan society of obstetrics and gynecology), (premenstrual syndrome: PMS), Jun. 16, 2018, cited in ISR.

* cited by examiner

FIG. 2

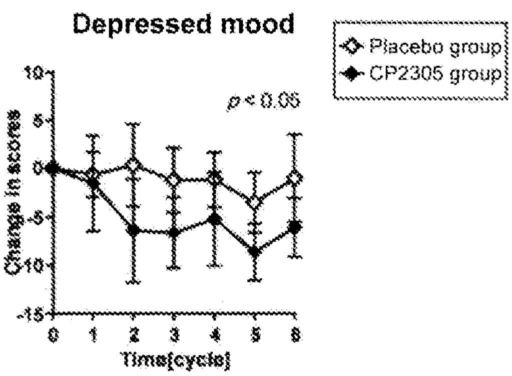

means ± SEM
A change from the pre-ingestion score was used for comparison between the groups by repeated measures ANOVA

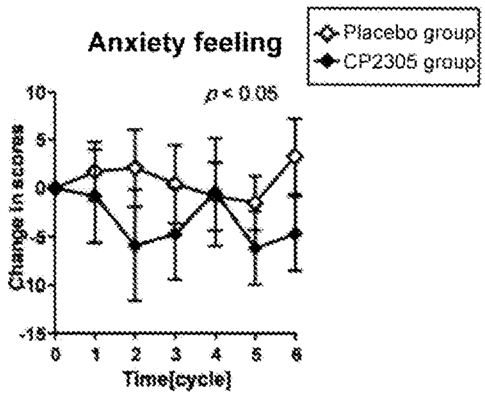

means ± SEM
A change from the pre-ingestion score was used for comparison between the groups by repeated measures ANOVA

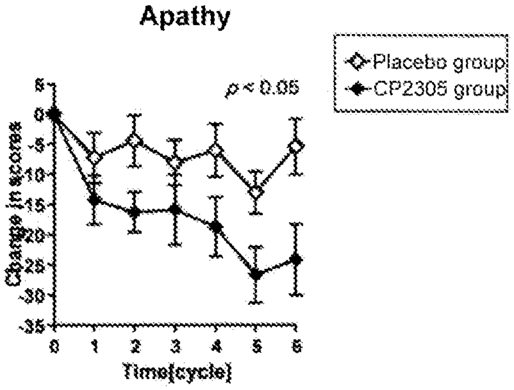

means ± SEM
A change from the pre-ingestion score was used for comparison between the groups by repeated measures ANOVA

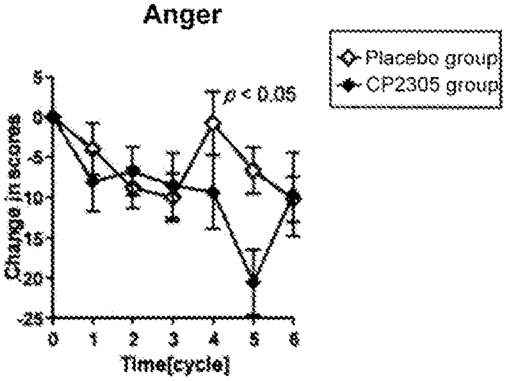

means ± SEM
A change from the pre-ingestion score was used for comparison between the groups by repeated measures ANOVA

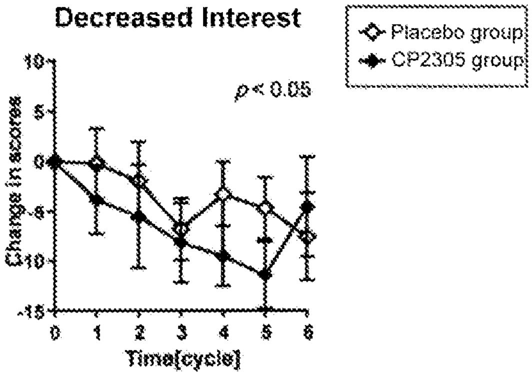

means ± SEM
A change from the pre-ingestion score was used for comparison between the groups by repeated measures ANOVA FIG. 3
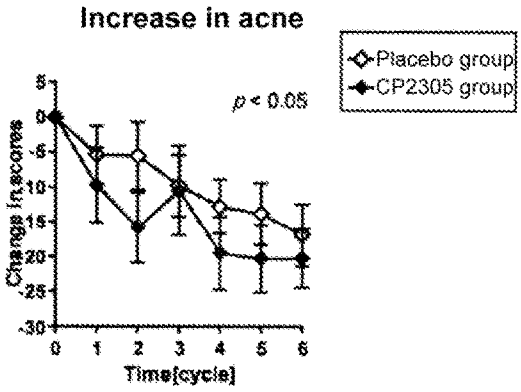
means ± SEM
A change from the pre-ingestion score was used for comparison between the groups by repeated measures ANOVA
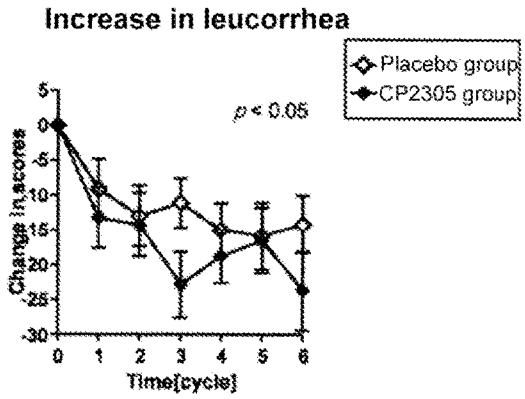
means ± SEM
A change from the pre-ingestion score was used for comparison between the groups by repeated measures ANOVA

AGENT FOR REGULATING FEMALE HORMONE SECRETION AND AGENT FOR ALLEVIATING UNPLEASANT SYMPTOMS

TECHNICAL FIELD

The present invention relates to a female hormone secretion regulating agent and an unpleasant symptom alleviating agent comprising a lactic acid bacteria that is *Lactobacillus gasseri* CP2305 strain, a processed product of the lactic acid bacteria, or an extract thereof.

BACKGROUND ART

It has been known that 80% of women who have menstrual cycles have premenstrual physical and/or mental unpleasant symptom (hereinafter, referred to as "premenstrual unpleasant symptom"). The premenstrual unpleasant symptom is considered to be symptom caused by the effects of female hormones.

When a given premenstrual unpleasant symptom appears repeatedly in consecutive menstrual cycles, it may be diagnosed as premenstrual syndrome (PMS) or premenstrual dysphoric disorder (PMDD), and may interfere with daily life. When the diagnosis of PMS or PMDD is made, counseling, lifestyle guidance, and diet therapy are generally followed by prescription of a selective serotonin reuptake inhibitor (SSRI) or low-dose pill as symptomatic therapy. The low-dose pill is a drug having female hormones as active ingredients, and alleviates symptoms by supplementarily supplying ex vivo produced exogenous female hormones.

Equol, a substance produced by intestinal bacteria, is known to show substantially the same effects as follicular hormone, a type of female hormone. Here, Patent Literature 1 discloses a technology using fermented soybean hypocotyl containing equol, produced by *Lactococcus* 20-92 strain, to improve menopausal disorder.

Note that menopausal disorder is menopause symptom that is seen mainly in women in their 40s and 50s and become so severe that they interfere with daily life. The main symptoms of menopause symptom are psychological symptom and autonomic dystonia, which are considered to be symptoms caused by a decrease in female hormones due to a decline in ovarian function.

CITATION LIST

Patent Literature

Patent Literature 1: JP 2014-158488A

SUMMARY OF INVENTION

Technical Problem

Like the above-described technology using a low-dose pill, the technology disclosed in Patent Literature 1 is a technology for alleviating (improving) symptom by supplementarily supplying an exogenous substance (equol) that acts as a female hormone, and is not a technology for regulating female hormone secretion.

The purpose of the present invention is to provide a novel technology allowing for regulation of female hormone secretion. In addition, another purpose of the present invention is to provide a novel technology allowing for alleviation of premenstrual physical and/or mental unpleasant symptom.

Solution to Problem

The present inventors have found that when a lactic acid bacteria that is *Lactobacillus gasseri* CP2305 strain, a processed product of the lactic acid bacteria, or an extract thereof is ingested, secretion of female hormones can be regulated. Thus, the present invention has been completed.

The gist of the invention is as follows.

[1] A female hormone secretion regulating agent comprising a lactic acid bacteria that is *Lactobacillus gasseri* CP2305 strain (accession number: FERM BP-11331), a processed product of the lactic acid bacteria, or an extract thereof.

[2] The female hormone secretion regulating agent according to [1], wherein the female hormone is luteinizing hormone and/or follicular hormone.

[3] A premenstrual physical and/or mental unpleasant symptom alleviating agent, comprising a lactic acid bacteria that is *Lactobacillus gasseri* CP2305 strain (accession number: FERM BP-11331), a processed product of the lactic acid bacteria, or an extract thereof.

[4] The alleviating agent according to [3], wherein the unpleasant symptom is premenstrual syndrome and/or premenstrual dysphoric disorder.

[5] The alleviating agent according to [3], wherein the unpleasant symptom is at least one symptom selected from the group consisting of depressed mood, anxiety feeling, apathy, anger, an increase in acne, and an increase in leucorrhea.

[6] Use of a lactic acid bacteria that is *Lactobacillus gasseri* CP2305 strain (accession number: FERM BP-11331), a processed product of the lactic acid bacteria, or an extract thereof for regulation of female hormone secretion.

[7] Use of a lactic acid bacteria that is *Lactobacillus gasseri* CP2305 strain (accession number: FERM BP-11331), a processed product of the lactic acid bacteria, or an extract thereof for the production of a female hormone secretion regulating agent.

[8] A therapeutic and/or prophylactic agent for a disease, comprising a lactic acid bacteria that is *Lactobacillus gasseri* CP2305 strain (accession number: FERM BP-11331), a processed product of the lactic acid bacteria, or an extract thereof, wherein the disease is at least one disease selected from the group consisting of polycystic ovary syndrome, dysmenorrhea, premenstrual syndrome (PMS), and premenstrual dysphoric disorder (PMDD).

[9] Use of a lactic acid bacteria that is *Lactobacillus gasseri* CP2305 strain (accession number: FERM BP-11331), a processed product of the lactic acid bacteria, or an extract thereof for treatment and/or prevention of at least one disease selected from the group consisting of polycystic ovary syndrome, dysmenorrhea, premenstrual syndrome (PMS), and premenstrual dysphoric disorder (PMDD).

[10] Use of a lactic acid bacteria that is *Lactobacillus gasseri* CP2305 strain (accession number: FERM BP-11331), a processed product of the lactic acid bacteria, or an extract thereof for the production of a therapeutic and/or prophylactic agent for at least one disease selected from the group consisting of polycystic ovary syndrome, dysmenorrhea, premenstrual syndrome (PMS), and premenstrual dysphoric disorder (PMDD).

[11] Use of a lactic acid bacteria that is *Lactobacillus gasseri* CP2305 strain (accession number: FERM BP-11331), a processed product of the lactic acid bacteria, or an extract thereof for alleviating a premenstrual physical and/or mental unpleasant symptom.

[12] Use of a lactic acid bacteria that is *Lactobacillus gasseri* CP2305 strain (accession number: FERM BP-11331), a processed product of the lactic acid bacteria, or an extract thereof for the production of a premenstrual physical and/or mental unpleasant symptom alleviating agent.

Advantageous Effects of Invention

The invention makes it possible to provide a novel technology allowing for regulation of female hormone secretion. In addition, the invention also makes it possible to provide a novel technology allowing for alleviation of premenstrual physical and/or mental unpleasant symptom.

BRIEF DESCRIPTION OF DRAWINGS

FIG. 2 is graphs each showing a correlation between a change in the score of a premenstrual unpleasant mental symptom and the time.

FIG. 3 is graphs each showing a correlation between a change in the score of a premenstrual unpleasant physical symptom and the time.

DESCRIPTION OF EMBODIMENTS

First Embodiment

Figure 1:
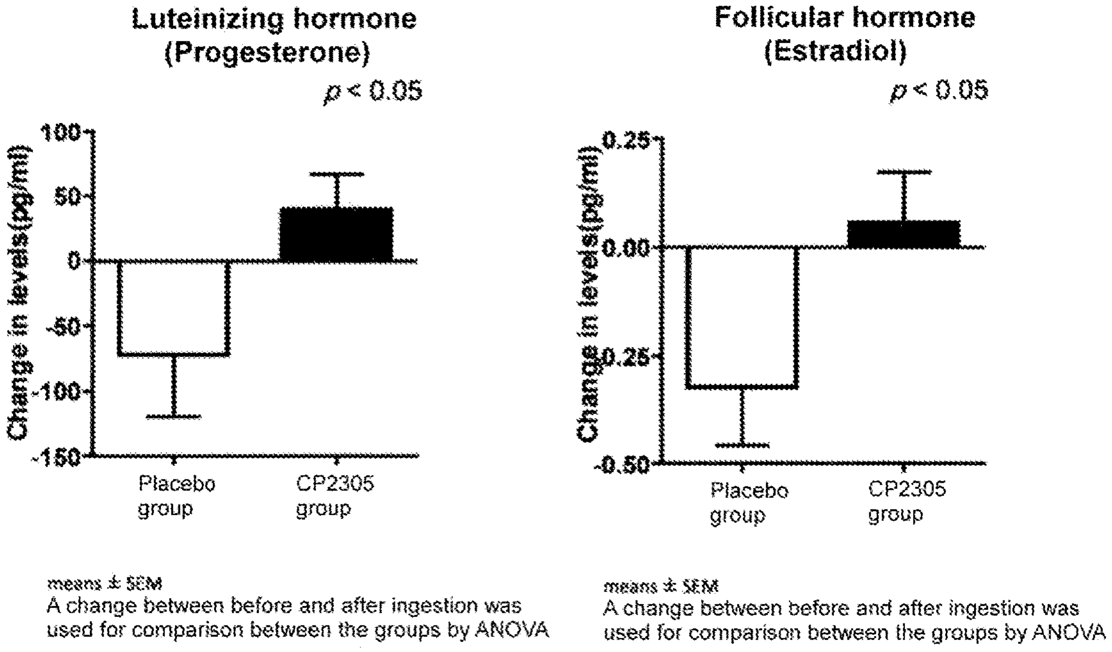
FIG. 1 is graphs showing a change in luteinizing hormone and a change in follicular hormone.

Hereinafter, the first embodiment of the invention will be described.

This embodiment pertains to a female hormone secretion regulating agent (hereinafter, also simply referred to as a "regulating agent"). A regulating agent of this embodiment comprises a lactic acid bacteria that is *Lactobacillus gasseri* CP2305 strain (hereinafter, also simply referred to as "CP2305 strain"), a processed product of CP2305 strain, or an extract thereof.

First, the CP2305 strain used in the regulating agent of this embodiment will be described specifically. Note that in the following description, CP2305 strain, a processed product of the CP2305 strain, and an extract thereof are also generally referred to as CP2305 strain, etc.

*Lactobacillus gasseri* CP2305 strain used in a regulating agent of this embodiment is a lactic acid bacteria and has been internationally deposited under accession number: FERM BP-11331, dated Sep. 11, 2007, in National Institute of Advanced Industrial Science and Technology, Patent Microorganisms Depositary (Tsukuba Central 6, 1-1-1 Higashi, Tsukuba, Ibaraki 305-8566 Japan), an international depository institution based on the provision in Budapest Treaty.

CP2305 strain used in the regulating agent of this embodiment is not particularly limited and as long as the CP2305 strain can grow in a medium, any medium may be used for culturing. For example, a CP2305 strain cultured in a medium generally used for culturing lactic acid bacteria (e.g., a synthetic medium such as MRS broth) may be used. It is also possible to use a CP2305 strain cultured in a modified version of that medium.

A nutrient used in a medium for culturing CP2305 strain is also not particularly limited if the CP2305 strain can grow.

Examples of a carbon supply source (hereinafter, also referred to as a "carbon source") that can be used include glucose, sucrose, lactose, or molasses, which can be utilized for routinely culturing microorganisms. Two or more of these carbon sources may be used in combination. In addition, examples of a nitrogen supply source (hereinafter, also referred to as a "nitrogen source") that can be used include peptone, casein, a casein degradation product, whey, or a whey degradation product. Two or more of these nitrogen sources may be used in combination.

A medium for culturing CP2305 strain optionally contains, in addition to the above carbon source and/or nitrogen source, another nutrient supply source. Example of such a nutrient supply source include corn steep liquor (CSL), yeast extract, meat extract, liver extract, or tomato juice. Two or more of these supply sources may be used in combination.

Further, the medium for culturing CP2305 strain optionally contains, in addition to the above-mentioned nutrient supply sources, other component(s) such as a reductant, a growth promoting factor, and/or a buffering substance. Specific examples of the reductant include L-cysteine. In addition, specific examples of the growth promoting factor include a vitamin, a nucleic acid-related substance, an acetate, a citrate, a fatty acid ester, or tween 80. Among them, tween 80 is more preferable. Specific examples of the buffering substance include a phosphate.

Any culture method for CP2305 strain can be used as long as the CP2305 strain can grow. Examples of the method that can be used include, but are not particularly limited to, static culture or neutralizing culture in which the pH is kept constant.

In the case of culturing CP2305 strain in a medium, the CP2305 strain may be harvested from the culture, and may then be used for a regulating agent of this embodiment. The harvest procedure is not particularly limited, and for example, centrifugation or membrane filtration may be used.

As described above, the regulating agent of this embodiment comprises CP2305 strain, a processed product of CP2305 strain (hereinafter, also simply referred to as a "processed product"), or an extract of CP2305 strain and/or a processed product thereof (hereinafter, also simply referred to as an "extract"). Specifically, the regulating agent of this embodiment comprises at least one of CP2305 strain, a processed product, or an extract.

For instance, viable cells, wet cells, or dried cells of CP2305 strain may be used for the CP2305 strain that can be included in the regulating agent of this embodiment.

For instance, a physically treated CP2305 stain processed product or a chemically treated CP2305 stain processed product may be used as the processed product that can be included in the regulating agent of this embodiment. Specific examples of the processed product include a CP2305 strain-containing fermented milk concentrate, a CP2305 strain-pasted product, a CP2305 strain-dried product, a CP2305 strain-liquified product, a CP2305 strain-diluted product, or a CP2305 strain lysate. Note that as the dried product, it is possible to use one dried product selected from the group consisting of spray dried products, freeze-dried products, vacuum-dried products, and drum-dried products.

The CP2305 strain in the processed product may be viable cells or dead cells. The dead cells may be obtained by heating bacteria cells. The heating conditions are not particularly limited if the bacteria cells are killed under the conditions. Generally, the bacteria cells are killed by heating at 105° C. for about 30 min. The procedure for obtaining dead cells is not limited to the above-mentioned heating procedure, and it is possible to use a procedure for killing bacteria cells by radiation or a procedure for killing bacteria cells by sonication.

An extract obtained by extracting CP2305 strain with a solvent may be used as the extract that can be included in the regulating agent of this embodiment. Examples of the solvent used for the extraction include, but are not particularly limited to, chloroform, ethyl acetate, hexane, diethyl ether, dimethyl sulfoxide, methanol, ethanol, water, or a mixture thereof. The extraction conditions such as an extraction temperature and an extraction period are not particularly limited, and it is possible to use common conditions for obtaining a bacteria cell extract.

The type (form) of the formulation of the regulating agent in this embodiment is not particularly limited, and any formulation type such as a pharmaceutical agent, a quasi-drug, or a food or drink may be adopted. Note that how to ingest the regulating agent of this embodiment may be set, if appropriate, depending on the type of the formulation, and is not particularly limited. For example, the regulating agent can be orally ingested.

The regulating agent of this embodiment optionally comprises, in addition to CP2305 strain, etc., an additional component(s) other than the CP2305 strain, etc. For example, the regulating agent of this embodiment may be provided as a pharmaceutical agent, a quasi-drug, or a food or drink. In this case, the regulating agent of this embodiment optionally comprises, in addition to CP2305 strain, etc., an additional component(s) such as an excipient, a binder, a stabilizer, a disintegrant, a lubricant, a flavoring agent, a suspending agent, a coating agent, a food, and/or a beverage.

The dosage form of the regulating agent in this embodiment is not particularly limited, and may be set, if appropriate, depending on the type of the formulation(form) of the regulating agent. In the case of providing the regulating agent of this embodiment as a pharmaceutical agent, a quasi-drug, or a food or drink, examples of the dosage form include a tablet, a pill, a capsule, granules, a spray, powder, or a syrup.

In the case of providing the regulating agent of this embodiment as a food or drink, a regular food or drink may be allowed, but the regulating agent may be provided as a food for special dietary uses or a food with nutrient function claims such as a food for specified health food. Specific examples of the food and drink include a nutraceutical (supplement), milk, processed milk, milk beverage, soft drink, fermented milk, yogurt, cheese, bread, cookie, cracker, pizza crust, ice cream, candy, gummy, gum, formulated milk powder, liquid diet, food for the sick, food for infants such as powdered milk, food for nursing mothers such as powdered milk, or feed.

The contained amount of CP2305 strain, etc., in the regulating agent of this embodiment is not particularly limited. For example, for an adults, the contained amount of CP2305 strain can be set to allow intake of 100 million to 100 billion cells of CP2305 strain (or an equivalent amount of CP2305 strain processed product or an equivalent amount of CP2305 strain extract) per day. The ingestion period of the regulating agent in this embodiment is not particularly limited, and may be, for instance, 6 or more consecutive menstrual cycles (i.e., consecutive 24 or more weeks).

The regulating agent of this embodiment as described above may be ingested to regulate female hormone secretion.

As used herein, the phrase "can regulate female hormone secretion" means that a change in the female hormone secretion amount (hereinafter, also referred to as the "female hormone amount") can be more moderate in the case of ingesting the regulating agent of this embodiment than in the case without ingesting the regulating agent of this embodiment. That is, a rapid change in the female hormone amount can be suppressed more in the case of ingesting the regulating agent of this embodiment than in the case without ingesting the regulating agent of this embodiment.

It is generally known that in the late luteal phase, the female hormone amount decreases and menstruation then occurs after this decrease in the female hormone amount. This decrease in the female hormone amount during the late luteal phase can be more moderate in the case of ingesting the regulating agent of this embodiment than in the case without ingesting the regulating agent. Thus, when the female hormone amount is compared during the same phase as in the late luteal phase, the female hormone amount is higher in the case of ingesting the regulating agent of this embodiment than in the case without ingesting the regulating agent of this embodiment.

Note that as used herein, the female hormone refers to luteinizing hormone (estrogen) and/or follicular hormone (progesterone). In addition, as used herein, the luteal phase refers to a phase from ovulation to the start of menstruation; and the late luteal phase refers to a later phase between two divided luteal phases.

In this embodiment, CP2305 strain, etc., may be used for regulating female hormone secretion or may be used for producing a female hormone secretion regulating agent. Specifically, one aspect of this embodiment includes use of CP2305 strain, etc., for regulation of female hormone secretion (use of a lactic acid bacteria that is *Lactobacillus gasseri* CP2305 strain, a processed product of the lactic acid bacteria, or an extract thereof) and use of CP2305 strain, etc., for the production of a female hormone secretion regulating agent (use of a lactic acid bacteria that is *Lactobacillus gasseri* CP2305 strain, a processed product of the lactic acid bacteria, or an extract thereof). Note that the CP2305 strain, etc., used for regulation of female hormone secretion or the CP2305 strain, etc., used for the production of a female hormone secretion regulating agent has the same configuration as for the CP2305 strain, etc., in the above-described regulating agent, and the detailed description is thus omitted.

In addition, as described above, the regulating agent of this embodiment can moderate a change in the female hormone amount. Because of this, the regulating agent of this embodiment can be used to treat or prevent diseases, whose symptom can be improved or onset can be prevented by moderating change in female hormone amount. Examples of such a disease include polycystic ovary syndrome, dysmenorrhea, premenstrual syndrome (PMS), or premenstrual dysphoric disorder (PMDD). That is, the regulating agent of this embodiment may be a therapeutic and/or prophylactic agent for at least one disease selected from the group (hereinafter, also referred to as the "disease group") consisting of polycystic ovary syndrome, dysmenorrhea, premenstrual syndrome (PMS), and premenstrual dysphoric disorder (PMDD) (the same configuration as for the regulating agent of this embodiment may be used to provide a therapeutic and/or prophylactic agent for at least one disease selected from the disease group).

In the above-described embodiment (therapeutic and/or prophylactic agent), CP2305 strain, etc., is used for treating and/or preventing at least one disease selected from the disease group. That is, one aspect of this embodiment includes use of CP2305 strain, etc., for treatment or prevention of at least one disease selected from the disease group (use of a lactic acid bacteria that is *Lactobacillus gasseri* CP2305 strain, a processed product of the lactic acid bacteria, or an extract thereof). Note that the CP2305 strain, etc., used for treating or preventing at least one disease selected from the disease group has the same configuration as for the CP2305 strain, etc., of the above-described regulating agent, and the detailed description is thus omitted.

Further, in the above-described embodiment (therapeutic and/or prophylactic agent), CP2305 strain, etc., is used for the production of a therapeutic and/or prophylactic agent for at least one disease selected from the disease group. That is, one aspect of this embodiment includes use of CP2305 strain, etc., for the production of a therapeutic and/or prophylactic agent for at least one disease selected from the disease group (use of a lactic acid bacteria that is *Lactobacillus gasseri* CP2305 strain, a processed product of the lactic acid bacteria, or an extract thereof). Note that the CP2305 strain, etc., used for the production of a therapeutic and/or prophylactic agent for at least one disease selected from the disease group has the same configuration as for the CP2305 strain, etc., of the above-described regulating agent, and the detailed description is thus omitted.

Second Embodiment

Next, the second embodiment of the invention will be described.

This embodiment relates to a premenstrual physical and/or mental unpleasant symptom alleviating agent. The alleviating agent of this embodiment comprises CP2305 strain, a processed product of CP2305 strain, or an extract thereof.

The alleviating agent of this embodiment has the same configuration as for the regulating agent of the first embodiment. Because of this, the detailed description about the configuration for the alleviating agent of this embodiment will be omitted. Note that the ingestion period and the ingestion method of the alleviating agent in this embodiment are the same as for the regulating agent of the first embodiment, and the detailed description is thus omitted.

The alleviating agent of this embodiment can provide a novel technology such that a premenstrual physical and/or mental unpleasant symptom(s) (hereinafter, also referred to as a "premenstrual unpleasant symptom") can be alleviated. That is, the alleviating agent of this embodiment may be ingested to alleviate a premenstrual unpleasant symptom.

Here, the premenstrual unpleasant symptom refers to a symptom(s) that appears in the luteal phase and is weakened or disappears during the menstruation period. That is, the premenstrual unpleasant symptom is a concept different from a symptom(s) that appears during the menstruation period of, for example, dysmenorrhea or a symptom(s) that is not weakened or does not disappear during the menstruation period with, for example, menopause symptoms.

The premenstrual unpleasant symptom is generally considered to be a symptom(s) caused by the effects of female hormones. The female hormone secretion would be regulated in the case of ingesting the alleviating agent of this embodiment as in the case of ingesting the regulating agent of the first embodiment, so that the premenstrual unpleasant symptom can be alleviated.

Note that the phrase "premenstrual unpleasant symptom can be alleviated" means that the premenstrual unpleasant symptom can be mitigated more in the case of ingesting the alleviating agent of this embodiment than in the case without ingesting the alleviating agent of this embodiment, and not necessarily refers to abolishing premenstrual unpleasant symptom.

Specific examples of the premenstrual unpleasant symptom that can be alleviated by the alleviating agent of this embodiment include depressed mood, anxiety feeling, apathy, or anger.

According to a publication ("Hyojun Seishin Igaku (Standard Psychiatric Medicine) 6th ed." (Igaku-Shoin Ltd.)), depressed mood can be defined such that the mood is deeply depressed without any reason. When a symptom of the depressed mood appears, one may feel, for example, depressed, sad, lonely, or disappointed, or one may lack self-confidence, have low self-esteem, and suffer from inferiority feelings.

According to the publication ("Hyojun Seishin Igaku (Standard Psychiatric Medicine) 6th ed." (Igaku-Shoin Ltd.)), anxiety feeling can be defined as a feeling of fear without any object. Note that according to this publication, in contrast to the anxiety feeling, phobias can be defined as a feeling of fear of objects. Symptom of anxiety feeling may appear and may be accompanied by various physical symptoms, such as palpitations (heartbeats), tightness in the chest, difficulty breathing, cold sweats, trembling, giddiness (dizziness), numbness in the hands and feet, weakness, frequent urination, thirst, difficulty sleeping, headache, etc.

According to a publication (Stahl's Essential Psychopharmacology, Neuroscientific Basic and Practical Applications, 4th edition (Medical Science International)), apathy can be defined as a lack of energy or motivation to do something. Symptom of apathy may appear and include, for example, decreased motivation, decreased spontaneity, less emotional upset, or decreased interest in surroundings.

According to the publication ("Hyojun Seishin Igaku (Standard Psychiatric Medicine) 6th ed." (Igaku-Shoin Ltd.)), anger can be defined as an increase in the excitability of emotions, and as a state of increased deep emotion due to displeasure over trivial matters.

In addition, examples of the other premenstrual unpleasant symptom that can be alleviated by the alleviating agent of this embodiment include premenstrual syndrome (hereinafter, also referred to as "PMS") and premenstrual dysphoric disorder (hereinafter, also referred to as "PMDD").

According to the diagnostic criteria of the American College of Obstetricians and Gynecologists as described in the Guidelines for Obstetrics and Gynecology, Gynecology Outpatient Edition 2017 (Japan Society of Obstetrics and Gynecology), PMS can be defined as "the presence of at least one of emotional symptom (mental discomfort) and physical symptom (physical discomfort) during the five days before menstruation in each of the last three consecutive menstrual cycles". Emotional and physical symptoms of PMS are described, for example, in the above-mentioned publication (Guidelines for Obstetrics and Gynecology, Gynecology Outpatient Edition 2017 (Japan Society of Obstetrics and Gynecology)).

Note that according to the above-mentioned publication (Guidelines for Obstetrics and Gynecology, Gynecology Outpatient Edition 2017 (Japan Society of Obstetrics and Gynecology)), the emotional and physical symptom(s) of PMS disappears within 4 days after the onset of menstruation and does not recur until at least the 13th day. In addition, the above-mentioned publication (Guidelines for Obstetrics and Gynecology, Gynecology Outpatient Edition 2017 (Japan Society of Obstetrics and Gynecology)) states that when symptom of PMS appears, there is a clear impairment in social, academic, or economic behavior and ability, and it can be understood that PMS is a premenstrual physical and mental symptom that interferes with daily life.

Meanwhile, according to the Guidelines for Obstetrics and Gynecology, Gynecology Outpatient Edition 2017 (Japan Society of Obstetrics and Gynecology), PMDD can be defined as a condition in which the main symptom is psychiatric symptom (emotional symptom (mental symptom)) and is stronger than those of PMS. PMDD can be diagnosed using, for example, the American Psychiatric Association's diagnostic criteria described in the above-mentioned publication (Guidelines for Obstetrics and Gynecology, Gynecology Outpatient Edition 2017 (Japan Society of Obstetrics and Gynecology)).

Further, examples of the other premenstrual unpleasant symptom that can be alleviated by the alleviating agent of this embodiment include an increase in acne or an increase in leucorrhea. Here, the increase in acne or leucorrhea refers to an increase in acne or leucorrhea during the premenstrual period (i.e., the luteal phase) compared to the period between the end of menstruation and the beginning of the luteal phase. Meanwhile, the leucorrhea is a product secreted from a female genital organ, and is commonly called vaginal discharge.

In this embodiment, CP2305 strain, etc., may be used for alleviating a premenstrual physical and/or mental unpleasant symptom or may be used for producing a for a premenstrual physical and/or mental unpleasant symptom alleviating agent. That is, one aspect of this embodiment includes use of CP2305 strain, etc., for alleviating a premenstrual physical and/or mental unpleasant symptom (use of a lactic acid bacteria that is *Lactobacillus gasseri* CP2305 strain, a processed product of the lactic acid bacteria, or an extract thereof) and use of CP2305 strain, etc., for the production of a premenstrual physical and/or mental unpleasant symptom alleviating agent (use of a lactic acid bacteria that is *Lactobacillus gasseri* CP2305 strain, a processed product of the lactic acid bacteria, or an extract thereof). Note that the CP2305 strain, etc., used for alleviating a premenstrual physical and/or mental unpleasant symptom or the CP2305 strain, etc., used for producing a premenstrual physical and/or mental unpleasant symptom alleviating agent has the same configuration as for the CP2305 strain, etc., of the above-described alleviating agent, and the detailed description is thus omitted.

EXAMPLES

Hereinafter, the invention will be described in more detail with reference to Examples. However, the invention is not limited to them.

[Study 1 (Female Hormone Amount)]

Heat-killed cells of CP2305 strain, maltose (excipient), dextrin (binder), starch (binder), and vegetable oil (lubricant) were mixed, and the resulting mixture was tableted (compression molded) to obtain round tablets with a diameter of 8 mm (hereinafter also referred to as "CP2305 tablets"). One CP2305 tablet weighed 0.22 g and contained about 5 billion CP2305 strain heat-killed cells.

In addition, by using the same procedure as for the CP2305 tablets, except that the amount of maltose was increased (by the same amount of the heat-killed cells) in place of the CP2305 strain heat-killed cells, round tablets with a diameter of 8 mm (hereinafter, also referred to as "Placebo tablets") were produced. Like the CP2305 tablet, one Placebo tablet weighed 0.22 g.

The CP2305 tablets and the Placebo tablets (hereinafter, they are also referred to as "tablets") were used to conduct a randomized placebo controlled trial (RCT) using a double-blind test. Specifically, 58 healthy women who have menstrual cycles (average age: 21 years old) were enrolled, grouped into two groups: a CP2305 tablet ingestion group (hereinafter, also referred to as "CP2305 group") and a Placebo tablet ingestion group (hereinafter, also referred to as "Placebo group"), and instructed to ingest two tablets daily during 6 consecutive menstrual cycles. Note that the day of the start of tablet ingestion is fixed to the day of the start of menstruation (the first menstruation).

For each of menstruation before the start of tablet ingestion (menstruation immediately before the first menstruation) and 6 consecutive menstruations after the start of tablet ingestion, each subject's saliva was collected 3 to 6 days before the start of each menstruation and the amount of female hormone (luteinizing hormone and follicular hormone) in the saliva collected was measured. Note that the amount of each female hormone was measured using a SALIVARY PROGESTERONE ENZYME IMMUNOASSAY KIT and SALIVARY 17β-ESTRADIOL ENZYME IMMUNOASSAY KIT from SALIMETRICS, Inc., in accordance with the recommended protocol.

Next, the value calculated by subtracting the female hormone amount before ingestion from the amount after tablet ingestion was used as a change in female hormone in each subject. The changes for each of CP2305 group or Placebo group were averaged, and how the tablet ingestion affected the female hormone amount at 3 to 6 days before the start of menstruation was measured. FIG. 1 show the results.

As can be seen in FIG. 1, the CP2305 group had a higher amount of any of luteinizing hormone and follicular hormone than a reference value (the female hormone amount before tablet ingestion). By contrast, the Placebo group had a lower amount of any of luteinizing hormone and follicular hormone than the reference value.

Premenstrual 3 to 6 days where saliva was collected fall under the late luteal phase as described above, and is a period during which the female hormone amount decreases in the case without any fertilized egg implantation. Thus, an increased female hormone amount during this period indicates a more moderate decrease in the female hormone amount. That is, as can be seen from the results shown in FIG. 1, the CP2305 tablet ingestion can make a decrease in the female hormone more moderate than Placebo tablet ingestion can.

[Study 2 (Premenstrual Unpleasant Symptom)]

A questionnaire was filled in during the tablet ingestion period and before the start of ingestion in the above-described Study 1. The questionnaire was used to evaluate the presence or absence of a premenstrual unpleasant symptom(s) during the luteal phase and their strength. The luteal phase immediately before each menstruation was evaluated for the total of 7 menstruations from the menstruation before tablet ingestion (menstruation immediately before the first menstruation) to the sixth menstruation after ingestion.

Specific premenstrual unpleasant symptoms evaluated in the questionnaire include seven items: depressed mood, anxiety feeling, apathy, anger, decreased interest, an increase in acne, and an increase in leucorrhea. Note that to clarify the term definitions, each subject was informed, prior to the questionnaire, of the definitions based on the above-described publications for evaluation items including depressed mood, anxiety feeling, apathy, and anger.

A Visual Analog Scale (VAS) was used to evaluate the presence or absence of a premenstrual symptom(s) and their strength in the questionnaire. In the VAS, the score at which the present symptom falls between score 0 and score 100 is filled in, with no symptom scoring 0 and a very strong symptom scoring 100.

Note that the evaluation items: depressed mood, anxiety feeling, and decreased interest among the questionnaire's evaluation items are PMTS-VAS evaluation items in a publication ("The premenstrual tension syndrome rating scales: an updated version.", Journal of Affective Disorders, 2011, Vol. 135, p 82-88), and are described as effective scales for PMS or PMDD screening.

FIG. 2 and FIG. 3 show the results. Note that the graphs shown in FIG. 2 and FIG. 3 each indicate a change in each score when the score in the questionnaire before tablet ingestion, which score should not be affected by the tablet ingestion, was set to a reference (a score change: 0). The abscissa represents menstrual cycles.

As shown in FIGS. 2 and 3, premenstrual unpleasant symptoms were significantly alleviated in the CP2305 group compared to the Placebo group in any of the evaluation items. The results showed that the CP2305 tablet ingestion can alleviate the premenstrual unpleasant symptoms, compared with Placebo tablet ingestion. Further, as the number of the menstrual cycles approached six, the premenstrual unpleasant symptoms tended to be more moderate.

The invention claimed is:

1. A method for regulating a female hormone secretion, comprising:

orally administering dead cells of *Lactobacillus gasseri* CP2305 strain accession number: FERM BP-11331 or a composition comprising the dead cells of *Lactobacillus gasseri* CP2305 strain accession number: FERM BP-11331 to a woman, wherein the woman has menstrual cycles, and the woman has at least one premenstrual symptom selected from the group consisting of apathy, anger and an increase in leucorrhea, to regulate the female hormone secretion of the woman.

2. A method for alleviating at least one of a premenstrual physical symptom and a premenstrual mental symptom, the method comprising:

orally administering dead cells of *Lactobacillus gasseri* CP2305 strain accession number: FERM BP-11331 or a composition comprising the dead cells of *Lactobacillus gasseri* CP2305 strain accession number: FERM BP-11331 to a woman, wherein the woman has menstrual cycles, and the woman has at least one premenstrual symptom selected from the group consisting of apathy, anger and an increase in leucorrhea, to alleviate at least one of the premenstrual physical symptom and premenstrual mental symptom.

3. The method according to claim 2, wherein the woman has premenstrual syndrome or premenstrual dysphoric disorder.

4. The method according to claim 2, wherein the at least one premenstrual symptom is an increase in leucorrhea.

5. The method according to claim 1, wherein the woman has premenstrual syndrome or premenstrual dysphoric disorder.

6. The method according to claim 1, wherein the at least one premenstrual symptom is an increase in leucorrhea.

7. The method according to claim 1, wherein the at least one premenstrual symptom is apathy.

8. The method according to claim 1, wherein the at least one premenstrual symptom is anger.

* * * * *